United States Patent [19]
Waits

[11] Patent Number: 5,593,445
[45] Date of Patent: Jan. 14, 1997

[54] BI-AXIAL PROSTHETIC JOINT

[76] Inventor: C. Thomas Waits, 305 Oak Ridge Dr., Pflugerville, Tex. 78660

[21] Appl. No.: 409,746

[22] Filed: Mar. 24, 1995

[51] Int. Cl.$^6$ .................................................. A61F 2/30
[52] U.S. Cl. ............................... 623/18; 623/20; 623/22
[58] Field of Search ................................ 623/18, 20, 22, 623/21; 403/56, 76, 90, 120–22, 133, 135

[56] References Cited

U.S. PATENT DOCUMENTS

| | | | |
|---|---|---|---|
| 3,521,302 | 7/1970 | Müller . | |
| 4,031,570 | 6/1977 | Frey . | |
| 4,092,078 | 5/1978 | Klotz et al. | 403/221 |
| 4,714,476 | 12/1987 | Ranawat et al. | 623/21 |
| 4,778,472 | 10/1988 | Homsy et al. | 623/18 |
| 4,784,661 | 11/1988 | Beckenbaugh et al. | 623/21 |
| 4,784,663 | 11/1988 | Kenna | 623/22 |
| 4,813,961 | 3/1989 | Sostegni | 623/22 |
| 4,840,631 | 6/1989 | Mathys | 623/22 |
| 4,842,605 | 6/1989 | Sonnerat et al. | 623/22 |
| 4,917,701 | 4/1990 | Morgan | 623/16 |
| 4,919,668 | 4/1990 | Rosenbaum et al. | 623/18 |
| 5,092,898 | 3/1992 | Bekki et al. | 623/22 |
| 5,181,926 | 1/1993 | Koch et al. | 623/22 |
| 5,197,987 | 3/1993 | Koch et al. | 623/18 |
| 5,263,988 | 11/1993 | Huebner | 623/22 |
| 5,336,267 | 8/1994 | Kubein-Meesenburg et al. | 623/18 |
| 5,344,459 | 9/1994 | Swartz | 623/18 |

FOREIGN PATENT DOCUMENTS

0507645  10/1992  European Pat. Off. ............... 623/18

Primary Examiner—John G. Weiss
Assistant Examiner—Bruce E. Snow
Attorney, Agent, or Firm— Fitch, Even, Tabin & Flannery

[57] ABSTRACT

Bi-axial implants for the replacement of human joints which require multi-axis rotation and translation as well as for the replacement of anatomical ball and socket joints. A first member has a fixation element such as a stem for affixation to a first bone and a convex head, which head is received in a cavity in a second member having a concave surface which member is designed for attachment to a second bone. Located between the convex and concave surfaces is a ring bearing which forms a circular line of contact with the convex head and a circular line of contact with the concave surface. When a load is applied and transferred between the first and second members, the position of the ring bearing shifts to an alignment substantially transverse to the direction in which the load is being applied.

20 Claims, 4 Drawing Sheets

BI-AXIAL PROSTHETIC JOINT

FIELD OF THE INVENTION

The present invention generally relates to a prosthetic device for the replacement of a human joint. More particularly, it relates to replacement of a joint wherein multi-axis rotation and translation is desirable, such as the temporomandibular joint of the jaw, and to replacement of an anatomical ball and socket joint, such as the hip joint.

BACKGROUND OF THE INVENTION

Most people who have disease of the temporomandibular joint (TMJ) suffer from a myo-facial pain-dysfunction syndrome primarily as a muscle problem related to dental or skeletal malrelationships and tensional factors, or in some cases, as a reversible irritation in the joint. Most of these patients can be successfully treated using nonsurgical techniques. The remaining individuals with defective TMJ usually have an organic disease within the joint, usually osteoarthritis, or physical trauma, which often requires some form of surgical treatment and joint reconstruction.

Patients with severe destruction of the temporomandibular joint (TMJ) of the human jaw from rheumatoid arthritis, osteoarthritis, tumors, and physical trauma all manifest significant functional impairment and often pose difficult challenges in joint reconstruction.

Much of the TMJ surgery that has been performed to date has been the result of pathological arthritic changes within the joint, e.g., ankylosis, a bony or fibrous fusion of the condyle (ball) to the mandibular fossa (socket). The surgical technique most commonly employed for treatment of this condition is essentially a form of osteoarthrotomy. Other surgical techniques, variously favored for symptoms other than ankylosis, include condylectomy, high condylectomy, meniscus replacement and/or repair, and placement of various implant prostheses; see, for example, House L. R., et al., "Temporomandibular Joint Surgery: Results of a 14-year Joint Implant Study" *Laryngoscope*, 94:4, pp 534–538 (April 1984).

For many years, TMJ interpositional arthroplasty has been an accepted surgical modality in the treatment of severe ankylosis. Typically, an osteotomy is performed at or below the line of the joint, and this may be accompanied by a partial or total diskectomy. In such procedures, it has been common to utilize some form of implant or prosthesis, either within the fossa or upon the condylar stump, or both, in order to restore approximately correct anatomic interpositional fit.

Presently available TMJ prosthetic devices, when used as functioning joints, can result in the loss of adequate mechanical fit for proper jaw function caused by long term creep and flow of the construction material. The construction material subsequently becomes abraded by the passage over the rough condylar bone, thereby causing particles of the material to slough off and be dispersed into the surrounding tissue resulting in pathological sequelae which are manifested by destructive lesions of the mandibular condyle. These particles, unless they become walled off by fibrous connective tissue, can result in a foreign-body giant cell reaction and reactive synovitis.

The temporomandibular joint of the jaw is one example of two bi-axial joints arranged in a common plane. Due to the complex motion of bi-axial joints arranged in a common plane, which is unobtainable using conventional ball and socket prosthetic devices, there is a need for a maintenance-free bi-axial joint replacement device with favorable distribution of articulating forces and which enables pain-free use with natural dexterity to patients who have damaged or diseased TMJ.

Human anatomy is also composed of many singular ball and socket-type joints, for example, hip and knee joints which are also in frequent need of replacement due to physical trauma and disease. The artificial socket of a prosthesis for a hip reconstruction is commonly embedded in the pelvis while a ball element is attached to a stem for insertion into the femur. Prostheses of the hip ordinarily require a low friction seat between a spherical part replacing the head of the femur and its housing implanted in the pelvis of the patient. The femur bears the load transmitted to the pelvis of a hip joint during the normal slow pace of walking which is greater than the load of at least five times the patient's weight. Therefore, a low coefficient of friction as well as the capability of shock absorption is required in a hip prosthetic device because peak loads as high as seven to eight times the amount of the body weight may occur with normal gait. Long biofunctional life from hip prostheses is especially desirable because of the impossibility of periodic access to the joint, the physiological stress associated with the surgery and the corollary, prolonged immobility of the recipient. Artificial hip joints presently available frequently have contact surfaces that become deformed and are rendered dysfunctional through the prolonged cyclic application of load during normal use.

Examples of prostheses of this general type are shown in the following: U.S. Pat. No. 5,092,898, issued Mar. 3, 1992; U.S. Pat. No. 4,842,605, issued Jun. 27, 1989; U.S. Pat. No. 3,521,301, issued Jul. 21, 1970; U.S. Pat. No. 5,181,926, issued Jan. 26, 1993; U.S. Pat. No. 4,279,041, issued Jul. 21, 1981; U.S. Pat. No. 4,031,570, issued Jun. 28, 1977; U.S. Pat. No. 4,840,631, issued Jun. 20, 1989; U.S. Pat. No. 4,718,911, issued Jan. 12, 1988; U.S. Pat. No. 4,813,961, issued Mar. 21, 1989; and U.S. Pat. No. 4,524,467, issued Jun. 25, 1985, as well as U.K. Patent No. 1,189,325, issued Apr. 22, 1970; and U.S. Pat. No. 1,527,498, issued Oct. 4, 1978. These patents generally describe ball and socket joint prostheses having general variations of rolling ball bearings, or a retainer having a train of such balls or a internal bearing arrangement, or a plurality of small discs fitted between two generally hemispherical surfaces to facilitate sliding between the two members which tend to be of conventional structural design.

Conventional ball and socket joints largely comprise a noncompliant member which rotates within a compliant member. The compliant member is designed to slightly deform under applied load and thereby distribute the load over a somewhat larger area. However, the compliant members of conventional prostheses, typically as a result of wear, create a dispersion of small particles of the compliant material, which particles migrate into surrounding living tissue resulting in detrimental inclusions, inflammation and biological damage. Moreover, prior prostheses have not effectively distributed normal physiological load, thus daily wear of the artificial devices often significantly reduces the utility and comfort of the anatomical asset to the recipients. Furthermore, the need for shock absorption inherent in many anatomical areas occupied by natural joints has not been effectively addressed by embodiments of prior devices.

U.S. Pat. No. 5,336,267, issued Aug. 9, 1994, discloses an artificial joint which can be used as a hip or knee replacement wherein a relatively large pressure-distributing body which can completely fill the region between two spherical surfaces, e.g. one convex and one concave. The express purpose of the pressure-distributing body is to distribute the forces in the joint over the functional surfaces. Although theoretically capable of undergoing more complex articulations, the illustrated joints are not self-aligning as there is no motive force to cause the pressure-distributing body to move and do not alleviate other undesirable aspects of the prior art prosthetic joints.

Therefore, there remains a need for a maintenance-free bi-axial joint replacement device having favorable distribution of articulating forces and inherently good lubricating properties, which device should enable patients who have damaged or diseased joints to achieve pain-free use with natural dexterity. Accordingly it is the object of the present invention to provide an improved bi-axial joint prosthesis which allows essentially original and natural physiological function of the damaged joint. This and other objects of the invention will be readily apparent from the following detailed description and the accompanying drawings.

SUMMARY OF THE INVENTION

A bi-axial prosthetic device is provided having extended range of motion in artificial joints, increased load distribution, shock absorption, prolonged wear, and ease of use wherein a convex head member contacts a concave shell member through a ring-shaped bearing. The articulation of the bi-axial prosthetic device is especially useful for replacement of human anatomical joints, such as the temporomandibular joint of the jaw, which require multi-axis rotation as well as translation. The improved prosthetic device is also especially useful for replacement of anatomical ball and socket joints, such as the human hip joint.

DETAILED DESCRIPTION OF PREFERRED EMBODIMENTS

The present invention provides a bi-axial prosthetic joint which can be employed for tandem use in the replacement of the human TMJ as well as for singular use in replacing anatomical ball and socket joints such as the human hip joint. A pair of these joints in dual arrangement may be used as a wrist prosthesis.

Figure 1:
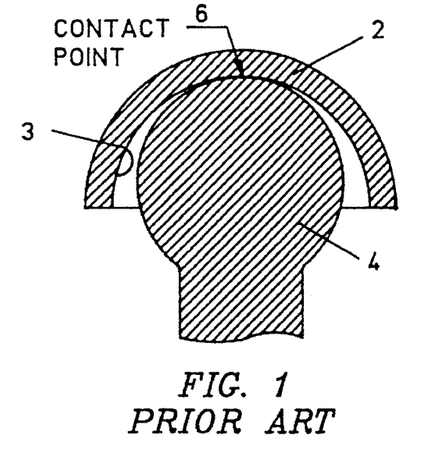
FIG. 1 is a schematic sectional view of a conventional ball and socket prosthetic joint.

Conventional ball and socket joints in widespread use today, an example of which is shown in FIG. 1, generally employ a socket element 2 having a spherical cavity 3 of a diameter that is slightly larger than that of a ball 4 at the end of the cooperating member; therefore, contact between the ball and socket generally occurs at a point 6 and yielding relatively poor distribution of an applied load and resulting in minimal shock absorption and heavy localized wear. The ball and socket members are respectively affixed to first and second bones in the body of the patient. Even if a somewhat compliant interior liner is provided in the socket, there is still fairly poor distribution of applied load which can result in localized stress upon the bone in contact that may lead to bone resorption, fibrous encapsulation, loosening, extrusion and failure of the material, as well as even eventual dislocation of the prosthesis.

Figure 2:
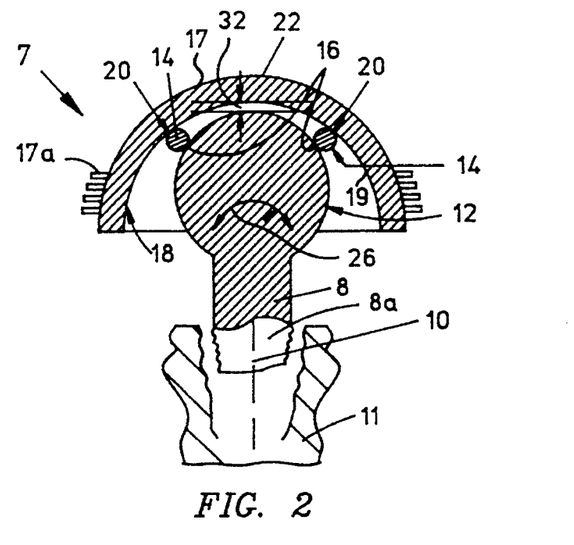
FIG. 2 is a similar sectional view which shows a basic bi-axial prosthetic joint embodying various features of the invention in which a first member having a spherical head is supported by a toroidal ring bearing within a second member having a hemispherical socket portion.

Illustrated in FIG. 2 is an improved bi-axial prosthetic joint 7 embodying various features of the invention. It comprises a first or condyle member 8 having some fixation means, such as a stem 8a, which is received in an appropriate cavity 10 fashioned in a first human bone 11 or the like, and having a convex generally spherical head 12 on the opposite end. A ring bearing 14 is in contact with the convex head along a proximal or first ring of contact 16 generally along a circular line. A second or fossa member 17 is formed with a concave shell portion 18 having a generally smooth interior surface 19 which receives the ring bearing 14 and the head 12; the fossa member 17 is suitably affixed to a second bone in the patient. There is a second ring of contact 20 between a radially exterior location on the ring bearing and the concave surface 19. The second member 17 is also designed for suitable attachment to human bone as well known in the art, see e.g. U.S. Pat. No. 4,031,570, the disclosure of which is incorporated herein by reference; for example, it may be formed with a series of grooves and ridges 17a.

The bi-axial prosthetic joint 7 effectively distributes the biomechanically applied load over a minimum of six points. The ring bearing 14 slides and shifts within the device but always contacts the concave surface 19 of the shell portion 18 at a minimum of three points along the ring of contact 20. The convex head 12 similarly contacts the ring bearing 14 at a minimum of three points along its respective ring of contact 16 therewith.

The embodiment of the present invention shown in FIG. 2 preferably employs a toroidal ring bearing 14 of circular cross-section interposed between a spherical head 12 and a hemispherical surface in the shell 18. The toroidal ring bearing is such that it simultaneously forms a first circular line of contact 16 with the spherical head 12 and a second circle of contact 20 with the hemispherical surface 19 of the shell portion 18. The toroidal ring bearing 14 maintains a minimum separation between the spherical head and the hemispherical shell, equal to the distance 32, in which region synovial fluid is accommodated.

The articulation between the head member 12 and shell portion 18 of the bi-axial prosthetic joint is effected as the ring bearing 14 slides and rotates about a center which is generally the center of the sphere of which the concave interior surface 19 of shell 18 is a section; the convex head 12 rotates about its own center while the location of such center generally constantly translates along an arc 26 so that its location at any time is determined by the position of the ring bearing 14. The position of the ring bearing 14 is dictated by the direction of the applied load (as explained hereinafter) and changes such that the planes of the circular lines of ring contact 16 and 20 are substantially perpendicular to the applied load. The movement of the ring bearing along the surfaces of the head 12 and shell 18 during the functioning of the prosthesis serves to clear the travel path of any deposited material and to also transport synovial fluid to these surfaces, which acts as a lubricant thus reducing friction and wear. Embodiments of alternative ring bearings are described below which act to positively pump synovial fluid across the contact surfaces of the members, thus further assuring lubrication and minimizing the build-up of residual deposits. This action eliminates the condition of a "dry joint" which tends to result in high friction and wear, as well as an uncomfortable grinding and/or "squeaky" sensation to the recipient.

Figure 3:
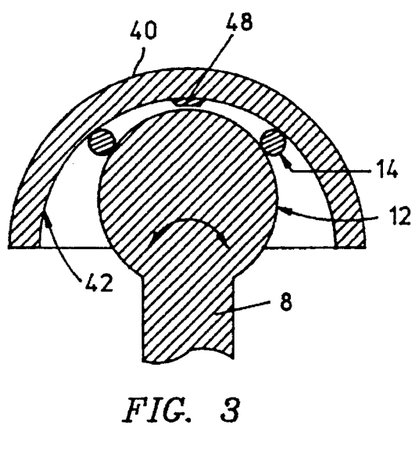
FIG. 3 is a sectional view, similar to FIG. 2, of another embodiment of a bi-axial prosthetic joint embodying various features of the invention wherein the interior surface of the concave shell portion has a protrusion, located interior of the ring bearing, which limits the travel of the ring bearing.

An alternative embodiment of a bi-axial prosthetic joint is shown in FIG. 3, the head 12 and ring bearing 14 are generally as hereinbefore described. However, a second member shell portion 40 is employed wherein its interior concave surface 42 has a protrusion 48 which limits the travel of the ring bearing 14. The first member having the head 12 and the second member shell portion 40 are preferably made of suitable biologically inert and corrosion-resistant material, such as a titanium alloy or a dense ceramic material. High strength chromium-cobalt-molybdenum alloys sold under the trademark "Vitallium" are often employed. The illustrated protrusion from the smooth concave surface 42 is located centrally within the hemispherical shell so its lies interior of the ring bearing. The protrusion 48 may be generally circular, or may have any other suitable geometric shape, and it preferably has a concave edge, with the radius of curvature of such concavity being about equal to the radius of the ring bearing circular cross section.

The ring bearing component of the bi-axial joint is preferably composed of a material having some lubricating properties, e.g., a pyrocarbon/graphite composite. The presently preferred composite for the ring bearing is a graphite substrate coated with pyrolytic carbon. Other preferred materials for construction of the ring bearing include those from which the first and second members can be made along with other suitable materials; examples include ultra high molecular weight polyethylene, titanium alloys, chromium cobalt alloys, tantalum, Vitallium®, aluminum oxide, molybdenum alloys, and stainless steel. Generally, any sufficiently rigid, biocompatible material that can be fashioned to fit the physical characteristics described herein may be used to construct the ring bearing; however, the bearing is preferably composed of a material which is different from that from which the head or the shell is constructed. The ring bearing is most preferably composed of pyrocarbon-coated graphite, but it may be formed from any biocompatible material with an appropriate modulus of elasticity that is sufficiently resistant to cyclic fatigue and which will maintain the integrity of the surface.

Figure 4:
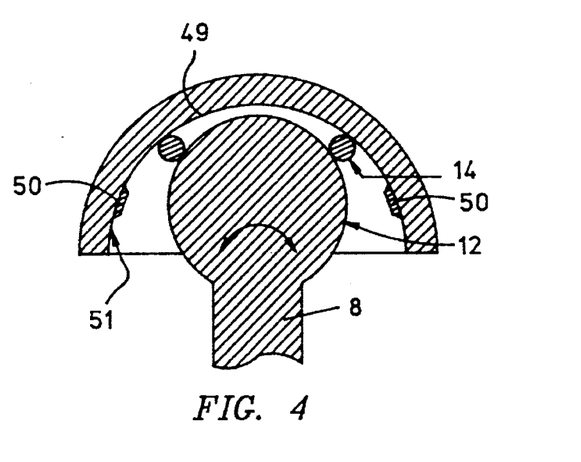
FIG. 4 is a sectional view, similar to FIG. 2, of still another embodiment of a prosthetic joint embodying various features of the invention wherein protrusion means is located exterior of the perimeter of the ring bearing and similarly limits the travel of the ring bearing.

Another alternative prosthetic joint is shown in FIG. 4 wherein a second member 49 also incorporates protrusion means 50 extending from the interior concave surface of the shell to limit the travel of the ring bearing 14. In this arrangement, such protrusion means may be a raised band 50 that encircles the shell, or a series of spaced-apart circular protrusions 50 which are all located at about the same latitude on an otherwise hemispherical surface 51. For example, there may be 6 individual protrusions 50 located at 60° spaced-apart intervals about the interior concave surface 51 of the shell portion of the second member 49. In this embodiment, these protrusions exterior of the ring bearing 14 prevent its displacement too far to one side or the other and thereby assure that the ring bearing remains centrally located in order to function in its optimal fashion.

Figure 5:
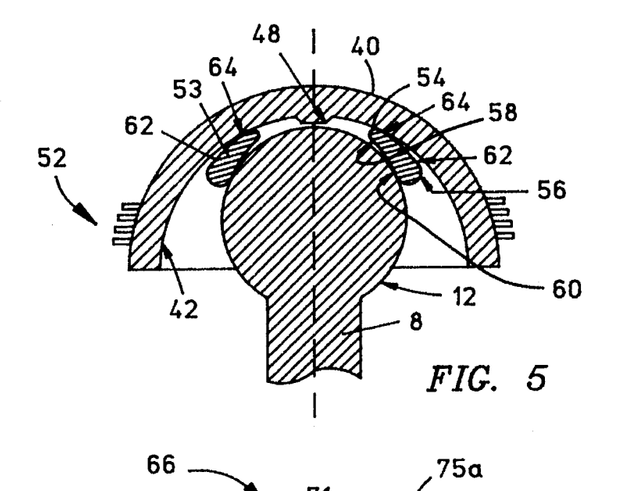
FIG. 5 is a sectional view of yet another embodiment of a prosthetic joint embodying various features of the invention showing a ring bearing having a teardrop cross sectional shape, with the wider end facing outward, wherein there is normal contact between the concave shell portion and the interior perimeter of the ring bearing.

Illustrated in FIG. 5 is another embodiment of a prosthetic joint 52 which employs a first member 8 having a spherical head 12 as described hereinbefore and a second member 40 having a central protrusion 48 extending inward from the interior surface 42 as generally described with respect to FIG. 3. A ring bearing 53 is utilized that is generally teardrop-shaped in cross-section having a narrow radially interior section 54 and a wide radially exterior section 56. The ring bearing 53 is shaped so as to contact the interior concave surface 42 of the shell portion only at a location near the narrow radially interior section 54 and so as to contact the convex surface of the spherical head 12 only at a location near the wide radially exterior section 56 of the ring bearing. As a result, under essentially no load conditions, the only contact between the ring bearing 53 and the head 12 and the shell surface 42, respectively, is along a first circular line of contact 60 with the head 12 and a second circular line of contact 64 with the shell surface 42, so that there is clearance in a region 58 between the narrow section 54 of the ring bearing and the ball, and there is clearance in a region 62 between the wide end 56 of the ring bearing and the concave surface of the shell portion. As a result, the shape of such a ring bearing 53 enables the bi-axial prosthetic device 52 to maintain minimal contact and thus minimize friction under lightly loaded conditions, to distribute high loads over a fairly large area, and to absorb kinetic shock through the energy required to deform the bearing.

Depending upon the material from which the ring bearing 53 is constructed, upon the application of relatively heavy loads, the thickness of the first line of contact 60 between the head 12 and the ring bearing 53 and the second line of contact 64 between the narrow section of the ring bearing and the concave shell surface may increase substantially;

however, the ring bearing 53 is preferably constructed of a material with sufficient rigidity that some clearance will always be maintained under normal physiological load so that the ring bearing will continue to assure the distribution of the lubricating synovial fluid and will also continue to shift to assume the desired orientation essentially transverse to the direction of the applied load as discussed hereinafter. Therefore, although different physical embodiments of the ring bearings are contemplated, in each instance the physical characteristics of the materials of construction are carefully considered, and the ring bearing is constructed and shaped to accommodate the expected anatomical load while conforming to the specifications set forth herein.

Figure 6:
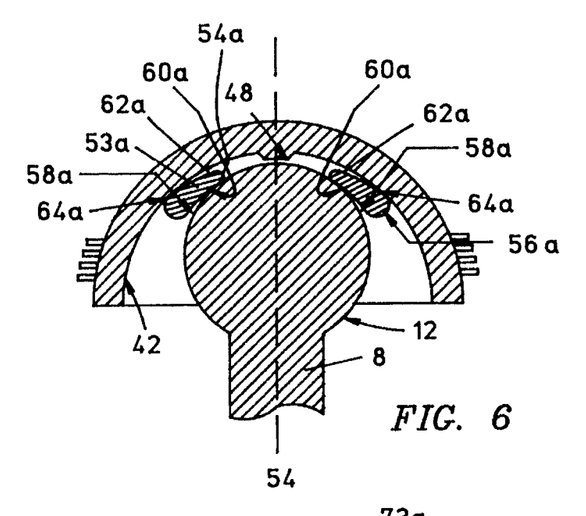
FIG. 6 is a sectional view similar to FIG. 5 showing another prosthetic joint embodying various features of the invention wherein a similar ring bearing is constructed so that the exterior perimeter of the ring bearing is normally in contact with the concave shell.

Illustrated in FIG. 6 is another alternative version of the prosthetic joint 52 depicted in FIG. 5 wherein items of the same construction are given the same reference numerals; the only difference lies in the construction of the ring bearing. A ring bearing 53a is illustrated where the shape of the ring bearing is slightly different so that the contact between the ring bearing and the head 12 is adjacent the narrow end 54a of the ring bearing and the contact between the ring bearing and the concave shell surface 42 is along the wide end 56a of the ring bearing. As a result, under essentially no load conditions there is a first circular line of contact 60a between the narrow end of the ring bearing and the head and a second circular line of contact 64a between the ring bearing and the concave shell. Accordingly, there is a region of clearance 62a at the narrow end of the ring bearing adjacent the concave shell surface 42, and there is a region of clearance 58a at the wide end of the ring bearing adjacent the head 12. Again, the ring bearing 53a is constructed of a suitable material such as a pyrocarbon-coated graphite substrate so that, even under the highest expected applied load, a substantial clearance remains although the lines of contact may grow substantially thicker as a result of some deformation.

Figure 7:
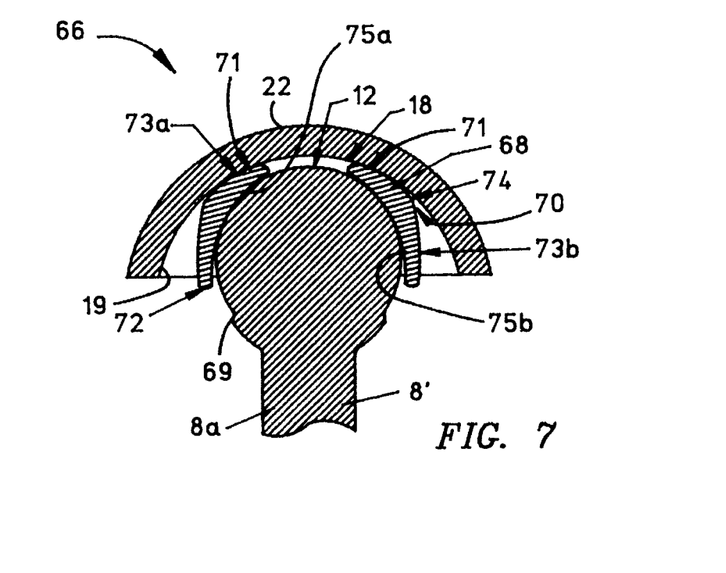
FIG. 7 is a sectional view of yet another bi-axial prosthetic joint embodying various features of the invention shown under minimum load wherein a wide ring bearing is used which extends past the equator of a head to terminate in a base opening having a diameter that is smaller than the maximum diameter (equator) of the head.
Figure 8:
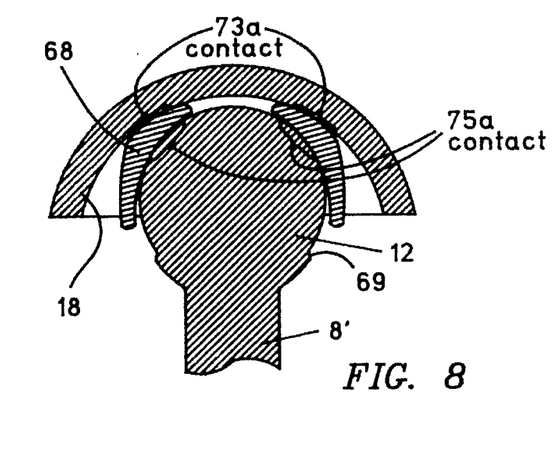
FIG. 8 is a view similar to FIG. 7 that shows the joint under maximum expected load.

Illustrated in FIGS. 7 and 8 is still another embodiment of a prosthetic joint 66 embodying various features of the invention which utilizes a shell or fossa member essentially the same as the member 22 illustrated in FIG. 2 and a first or condyle member 8' having a spherical head 12 and differing only in the inclusion of a collar 69 at the region where the head blends into the stem 8a of the structural member. A modified ring bearing 68 is used which is substantially wider than the previously described ring bearings and which is constructed so that at its base 72 there is an opening of a diameter less than the diameter at the equator of the head 12. As a result, when the ring bearing 68 is installed on the head 12 of the first member 8', it essentially snaps in place after undergoing a slight expansion when the base end of the ring bearing slides over the equator of the head. The lower projecting collar 69 limits the travel of the ring bearing, much as did the protrusion means 50 as shown in FIG. 4, and assures that the ring bearing 68 stays substantially centered with respect to the head 12.

The ring bearing 68 is designed with its thickest portion located at a central section 70 with both the upper and lower ends, 71 and 72, respectively, being substantially narrower. Moreover, the shape of the ring bearing 68 is such that it has a pair of radially exterior convex surfaces 73a and b which extend from a central ridge 74 at the point of greatest thickness and a pair of radially interior concave surfaces 75a and b. The precise proportioning and orientation of the 4 arcuate surfaces is such that the only contact between the ring bearing 68 and the interior concave surface 19 of the shell in the unloaded condition occurs along the ridge 74, and the only contact between the ring bearing and the spherical convex surface of the head 12 appears along a circular line near the narrow radially inward end 71. Accordingly, under unloaded conditions, there is clearance along both the radially inward convex surfaces 73a and the radially outward convex surface 73b of the ring bearing, and there is also clearance along substantially the entire radially inward concave surface 75a and all of the radially outward concave surface 75b. The ring bearing 68 is preferably constructed of material such as pyrocarbon/graphite composite, that will undergo some deformation under increasing load and therefore increase the contact area and serve to further spread the load.

As shown in FIG. 8, when subjected to about the maximum expected load, the contact between the ring bearing 68 and the interior concave surface 19 of the shell member extends over essentially the entire radially inward convex surface 73a, and similarly, the contact between the ring bearing 68 and the spherical ball 12 extends over essentially the entire radially inward concave surface 75a, while clearance remains between the radially outward surface portion 75b and the ball. Moreover, these physical changes in the shape of the ring bearing 68 as a result of the amount of the applied load serve not only to absorb kinetic shock but also to act as a mechanical pump which promotes the circulation of synovial fluid in the region between the ball 12 and the surrounding shell 18, thus assuring that good lubrication exists which decreases friction and thus alleviates wear. Moreover, the discharge action of the fluid also acts generally like a hydraulic shock absorber.

Figure 9A:
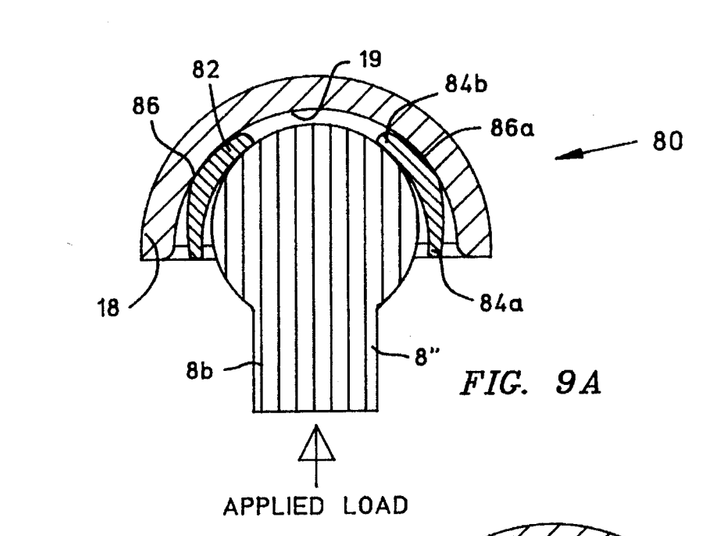
FIGS. 9A–9D disclose still another alternative embodiment of a prosthetic joint having general similarity to the joint disclosed in FIGS. 7 and 8, with the 4 different views illustrating load being applied to the joint in different directions in combination with the first member having different relative angular orientations with respect to the cup-like second member.
Figure 9B:
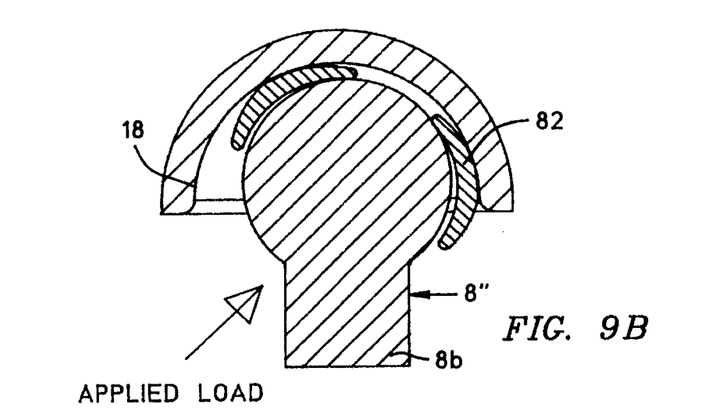

The self-alignment feature of a prosthetic joint bearing ring is illustrated using a joint very similar to that shown in FIGS. 7 and 8. As shown in FIGS. 9A, B, C and D, this prosthetic joint 80 utilizes a first member 8" having a spherical head which is similar to the head shown in FIG. 2 and a second shell portion member 18 with a concave generally hemispherical interior surface 19 essentially the same as the fossa member 22 of FIG. 2. A ring bearing 82 is used which is essentially the same as member 68 of FIG. 7. The diameter of the stem portion 8a is enlarged so as to be sufficient to limit the travel of the ring bearing 82 in the manner of the collar 69.

Figure 9C:
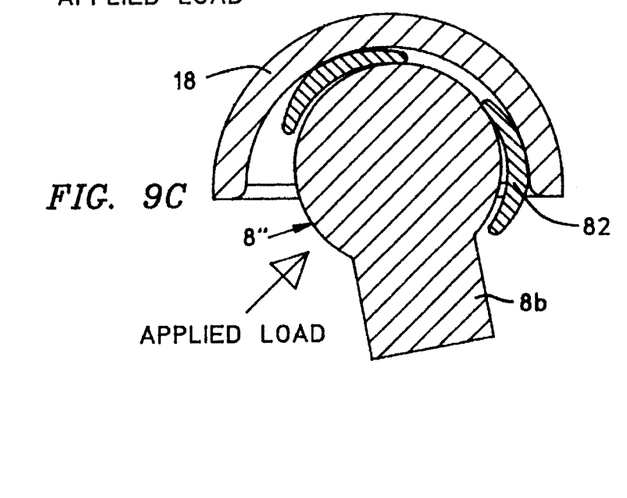
Figure 9D:
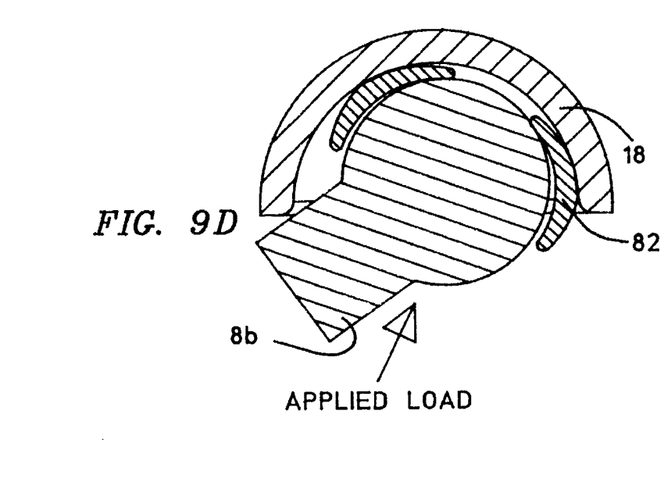

A particularly important self-aligning feature of the ring bearings of the invention is illustrated in connection with the embodiment of the joint 80; however, it should be understood that this is also considered to be an inherent feature of other of the ring bearings described in this specification. The construction of the ring bearing 82 is such that it has the propensity to align itself to an orientation transverse to the direction of the applied load. Therefore, regardless of the orientation of the stem portion 8b of the first member with respect to the shell portion, when the direction of loading changes, see FIGS. 9A and 9B, the ring bearing 82 rotates or pivots as a result thereof to assume the orientation shown in FIG. 9B which again is transverse or perpendicular to the direction of the applied load. Even if the first member 8" is pivoted counterclockwise as shown in FIG. 9C, so long as the applied load direction remains the same, the orientation of the ring bearing 82 does not change from that shown in FIG. 9B. This is also true if the first member 8" is rotated clockwise as far as possible, as shown in FIG. 9D; so long as the direction of the applied load does not change the orientation of the ring bearing 82 remains the same. This feature is considered to be an important advantage of these prosthetic joint constructions because, while there is substantial clearance provided in the region between the ball and the smooth concave surface of the shell in which synovial fluid can be accommodated to carry out the desired lubrication, the joint remains structurally stable regardless of the respective attitude of the two members and the direction of the applied load, and further because shock absorption, as a result of ring deformation, occurs in the direction of the applied load so that shock absorption is constant for a given load regardless of its direction. Moreover, because the ring aligns itself relative to the applied load, the motion of the joint remains predictable, whereas it would be random, dependent upon its present location, if it were not self-aligning.

All embodiments of the present invention which are described supra may be used in tandem arrangement to replace anatomical joints which require multi-axis rotation as well as translation such as the temporomandibular joint components of the human jaw. The temporomandibular joint of the human jaw is one example of two bi-axial joints arranged in a common plane. The TMJ anatomical components include the condyle (ball) which articulates with the mandibular fossa (socket). The convex head 12 and concave shell 18 of the bi-axial prosthetic joint described herein may be used to replace the condyle and the mandibular fossa of the human TMJ (see, e.g., Kent, J. N., et al., *Temporomandibular Joint Condylar Prosthesis: A ten Year Report*; J. Oral and Maxillofacial Surgery, vol. 41, 245–254 (1983)). The bi-axial prosthetic joint may be implanted and fitted to replace the natural TMJ according to present methods known to those skilled in the art. For example, these improved joints can be incorporated into replacements such as those illustrated in U.S. Pat. Nos. 4,778,472 and 4,917,701, the disclosures of which are incorporated herein by reference. A method for using tandem bi-axial prosthetic joints to replace anatomical joints which require multi-axis rotation as well as translation is accordingly contemplated.

Although the TMJ requires considerable translation, the human hip joint requires little or none. However, the bi-axial prostheses described herein are also considered useful for hip reconstruction wherein the attachment portion 22 of the concave shell is embedded in the pelvis and the convex head 12 is attached via insertion of a stem-like member into the femur. Standard methods may be used to attach the respective components of the present invention to the human bone anatomy (see, e.g. Ferrari, B. et al., The Journal of Bone and Joint Surgery, Vol. 68-A:8, 1117–1184 (1986)). For example, the intramedullary stem 8 of the first member can be attached to bones using any of several methods, such as: 1) bone growth into a porous coating or undulating surface of the intramedullary stem, 2) use of bone cement, 3) bonding of the intramedullary stem to bone by means of a surface active stem coating such as hydroxyapatite, and 4) a tight mechanical fit of the stem in the medullary cavity. The receiving cavity 10 in human bone is preferably reshaped during surgery, using a special broach, to achieve a snug fit for the stem 8 of the convex head 12 component. Radial protrusions or interlocking key shapes and the like can be used to enhance mechanical stability.

The exterior attachment surface of the second member 22 having the concave surface 19 can be attached to bone by means similar to 1–4 described supra for the stem portion of the head component; of course, the human jaw or the pelvis does not lend itself to accommodate a long intramedullary stem. For example, the second member which incorporates the concave shell 18 may be formed with a plurality of sharp ridges such as the ridges 17a depicted in FIG. 2 that protrude outward from the otherwise hemispherically shaped exterior surface portion, which ridges stabilize and tend to lock this cup-like member in a similarly cup-shaped depression created in the pelvis or jaw. Spike-shaped protrusions or interlocking key shapes and the like might also be used to enhance mechanical stability. Although the shell member 22 defining the concave surface 19 is preferably fashioned to fit into a cavity hollowed-out in a receiving bone, it may be otherwise shaped for attachment via a multitude of possible mechanisms such as are known to those skilled in this art. Attachment is possible, inter alia, via bone cement, tissue ingrowth, bonding to active materials such as hydroxyapatite, mechanical interlocking or a combination of any of these means. Irregularities on the surface such as ridges, grooves, dimples and undulations can be used to enhance attachment.

A variety of methods are known to those skilled in this art for physically interconnecting the first and second members to securely retain the convex head 12 of the first member within in the concave shell portion of the second member. Most preferably, a semi-constrained construction is used wherein the patient's own anatomy, i.e., muscles, tendons and ligaments, secure the elements of the bi-axial prosthetic joint together during use. When inserting the prosthetic joint, the surgeon aligns the elements as closely as possible within the patient's own natural anatomy. A cylindrical portion may be added, if desired, to extend the perimeter of the hemispherical shell for the purpose of increasing the depth of the shell and reducing its propensity toward dislocation.

Figure 10:
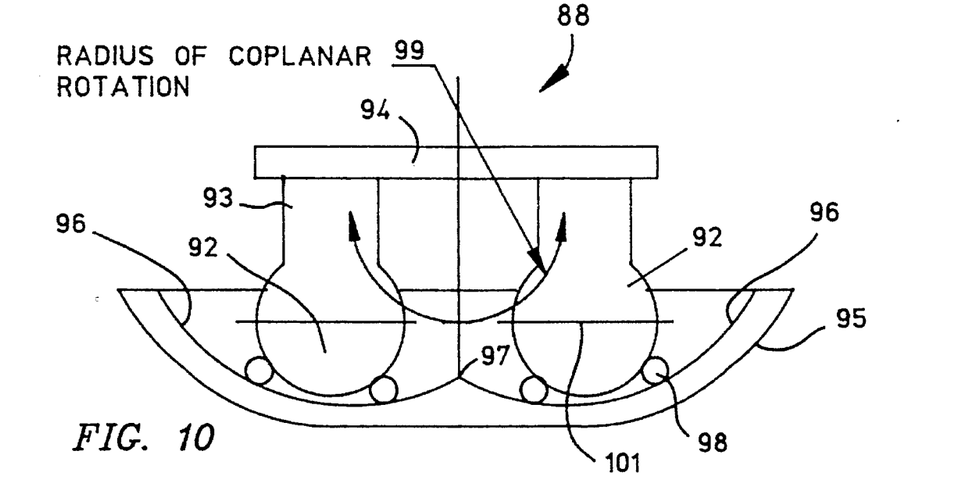
FIG. 10 is a sectional view of a simple dual arrangement of two bi-axial prosthetic joints embodying various features of the invention which arrangement exhibits different radii of articulation in different planes.
Figure 11:
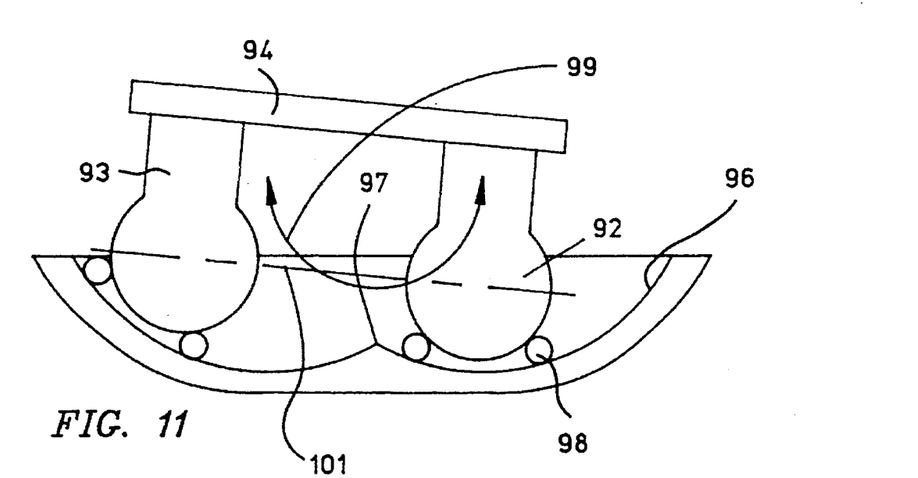
FIG. 11 is similar to FIG. 10 showing the same arrangement in a different position of orientation.

The prosthetic joints described hereinbefore enable articulation that permits simultaneous translation and rotation, which cannot be accomplished in a conventional ball and socket joint. A dual bi-axial prosthetic joint 88 is shown in FIGS. 10–11 which is considered to be especially well suited for the replacement of a joint, such as the human wrist or ankle, or another similar anatomical area wherein an even greater degree of translation and rotation may be desired. The arrangement generally includes a pair of individual bi-axial prosthetic joints 90 of similar shape and construction, placed side-by-side, as shown in FIG. 10, and it permits varying translation and rotational movement about different radii in different planes as can be seen by comparing FIGS. 10 and 11. Generally, the dual prosthetic joint 88 utilizes a pair of identical balls 92 of generally spherical shape having stem portions 93 that are affixed to a common base member or plate 94 such that the balls are affixed with their centers spaced a predetermined distance apart. The plate 94 is in turn suitably affixed to the bone or bones in question; such affixation can be accomplished using state-of-the-art arrangements such as those shown in U.S. Pat. Nos. 5,133, 762, 4,784,661 and 4,714,476, the disclosures of which are incorporated herein by reference.

Figure 10A:
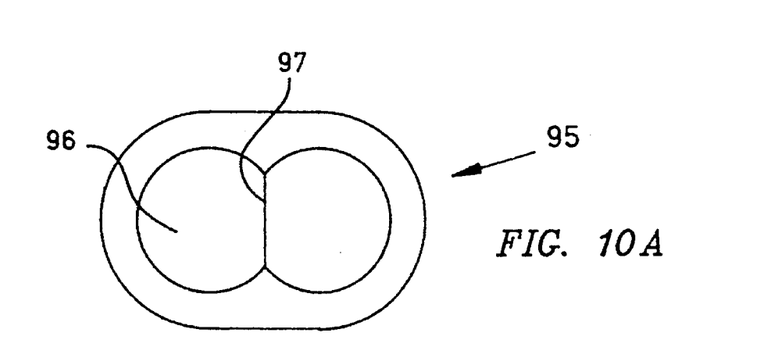
FIG. 10A is a plan view, reduced in size, of the second cup-like member by itself.

FIG. 10A is a plan view, reduced in size, of the second shallow cup member 95 which includes a pair of shallow spherical sector cavities 96 that intersect or overlap each other, sharing a common arcuate ridge 97. The distance between the centers of the spheres which define the spherical cavities 96 is preferably about equal to the predetermined distance between the centers of the balls 92. The pair of spherical heads 92 can move in various motions guided by ring bearings 98 and by the shape of the concave surfaces 96. For example, there can be simple rotational movement of the members of the joint about the vertical axis (as viewed in FIGS. 10 and 11). There can also be composite translational and pivoting movement in the plane of the paper as indicated by the arcuate arrows 99. Furthermore, there can be rotation in the plane perpendicular to the paper along an axis of rotation 101 which includes the centers of both heads 92. Of course, in addition to these three independent movements, there can be substantially any combination of two or more of these movements which, as can be seen, affords great latitude in the articulation movement between the two members. Although preferably both balls 92 are spheres having equal radii, if desired some changes in the radii could be employed to achieve a particular effect, or change might be made in the length of one of the stems. Changes in one of the radii would of course be preferably accompanied by changes in the corresponding ring bearing 98, although the concave surfaces 96 could also be sectors of spheres of slightly different radii. Although ring bearings 98 are illustrated which are similar to the ring bearings shown in FIG. 2, it should be understood that any of the various ring bearings described hereinbefore could instead be employed in such an arrangement.

The bearing surfaces of the components of the bi-axial prosthetic joint described herein are preferably vibratory-polished in such a manner so as to result in a slight waviness of the finished surfaces. These extremely shallow hills and valleys result in friction reduction by reducing contact area and also serve to capture and convey synovial fluid which acts as a natural lubricant. The articulating surfaces may also be coated with polyurethane, polyethylene or other biocompatible polymeric resins to prevent site-specific bone growth and to further reduce friction. The surface finish of all mating surfaces is preferably smooth enough to minimize wear, e.g., 16 micro inches or less.

Although the invention has been described with respect to preferred embodiments, various changes and modifications as would be obvious to one having ordinary skill in the art may be made without departing from the scope of the invention which is defined solely by the appended claims.

Particular features of the invention are emphasized in the claims which follow.

What is claimed:

1. A bi-axial prosthetic joint comprising
   a first member having means for fixation to a first bone and having a convex head,
   a second member which is shaped for attachment to a second bone and which includes a generally smooth concave surface portion of a size sufficient to receive said head, and
   a ring bearing which has a central opening and is shaped and proportioned to generally form a first ring of contact with said convex head of said first member and a second ring of contact with said concave surface of said second member, said ring bearing having sufficient rigidity such that some clearance will always be maintained under normal physiological load between facing surface portions of said first member head and said ring bearing adjacent said first ring of contact and between facing surface portions of said ring bearing and said second member concave surface adjacent said second ring of contact, and said ring bearing being free to shift and slide along said concave surface of said second member and along said convex head.

2. The bi-axial prosthetic joint of claim 1 wherein said convex head of said first member is generally spherical, said ring bearing is substantially toroidal, and said concave surface of said second member is a generally spherical surface.

3. The bi-axial prosthetic joint of claim 1 wherein said convex head of said first member and said concave surface of the second member are each generally spherical, and wherein said ring bearing has a pair of convex radially exterior surfaces, a concave radially interior surface and a central section that is thicker than the remainder of said ring bearing.

4. The bi-axial prosthetic joint of claim 3 wherein said pair of convex radially exterior surfaces meet in an intermediate circular ridge in said central section which ridge forms the sole line of contact between said ring bearing and said concave surface when the joint is substantially unloaded.

5. The bi-axial prosthetic joint of claim 4 wherein there is contact between said ring bearing and said convex head surface along said first ring of contact in the form of a circular line near the radially inward end of said ring bearing.

6. The bi-axial prosthetic joint of claim 5 wherein said first and second members are made of metal and said ring bearing is a substrate coated with pyrocarbon.

7. The bi-axial prosthetic joint of claim 1 wherein said generally smooth surface of said second member has formed therein a protrusion which is located interior of said ring bearing, which protrusion limits the extent of travel of said ring bearing in the region between said convex head and said concave surface of said second member.

8. The bi-axial prosthetic joint of claim 1 wherein said generally smooth surface of said second member has formed therein protrusion means which is located exterior of said ring bearing, which protrusion means limits the extent of travel of said ring bearing in the region between said convex head and said concave surface of said second member.

9. The bi-axial prosthetic joint of claim 1 wherein said head of said first member is generally spherical, said ring bearing has such a width that it extends past the equator of said head of said first member and terminates in a circular base opening having a diameter that is smaller than the diameter at the equator of said generally spherical first member so that said ring bearing base opening is momentarily expanded when said ring bearing is snapped into place onto said first member.

10. The bi-axial prosthetic joint of claim 9 wherein protrusion means exists near the base of the first member which limits the travel of said ring bearing, and wherein said ring bearing is constructed of material such that, under increasing load said ring bearing is deformed to increase its contact area with both said first member and said second member.

11. A method of replacement of the temporomandibular joint components of the human jaw, which method comprises providing a pair of bi-axial prosthetic joints according to claim 1 and implanting said pair of the bi-axial prosthetic joints of claim 1 which provide multi-axis rotation as well as translation, one such joint on the right side and one on the left side of the jaw.

12. A composite bi-axial prosthetic joint which comprises a first member having a pair of generally spherical convex heads which are located a predetermined distance from each other, both being affixed to a common base means that is designed for attachment to a first bone,
   a second member which is attachable to a second bone and which includes a pair of adjacent concave surfaces shaped and proportioned to receive said pair of heads, and
   a pair of separate ring bearings, each having a central opening, respectively positioned between one of said heads and one said concave surface of said second member, each of said ring bearings generally having a first ring of contact with said respective convex head and a second ring of contact with said respective concave surface of said second member and being free to separately shift relative to both said respective convex head and said concave surface, and each said ring bearing having sufficient rigidity such that some clearance will always be maintained under normal physiological load between facing surface portions of said first member head and said ring bearing adjacent said first ring of contact and between facing surface portions of said ring bearing and said second member concave surface adjacent said second ring of contact.

13. The composite joint according to claim 12 wherein said concave surfaces are essentially surfaces of a pair of spheres, the centers of which are located said predetermined distance apart.

14. The composite joint according to claim 13 wherein the radii of said pair of heads are substantially equal.

15. A bi-axial prosthetic joint comprising a first member having means for fixation to a first bone and having a convex head, a second member which is shaped for attachment to a second bone and which includes a generally smooth concave surface portion of a size sufficient to receive said head, and a ring bearing which is generally teardrop-shaped in cross-section having a wide section and a narrow section, said ring bearing being free to shift relative to said concave surface and to said convex head and being proportioned and shaped so that, under essentially no load, said wide section forms one ring of contact with one member of (a) said first member head and (b) said second member concave surface and is out of contact with the other member thereof, and said narrow section forms another ring of contact with said other member of (a) and (b) and is out of contact with said one member of (a) and (b), whereby clearance exists between said first and second members and said ring bearing except for said two rings of contact.

16. The bi-axial prosthetic joint of claim 15 wherein said ring bearing is proportioned and shaped so that, under essentially no load, said wide section is in contact with said convex head of said first member and out of contact with said concave surface of said second member and said narrow section is in contact with said concave surface of said second member and out of contact with said convex head.

17. The bi-axial prosthetic joint of claim 16 wherein said wide section is located radially outward in the structure of said ring bearing and said narrow section is located radially inward in the structure of said ring bearing.

18. The bi-axial prosthetic joint of claim 15 wherein said ring bearing is constructed of material having sufficient rigidity such that some clearance will always be maintained under normal physiological load between facing surface portions of said first member head and said ring bearing adjacent said ring of contact therebetween and between facing surface portions of said ring bearing and said second member concave surface adjacent said ring of contact therebetween.

19. The bi-axial prosthetic joint of claim 15 wherein said ring bearing is proportioned and shaped so that, under essentially no load, said wide section is in contact with said concave surface of said second member and out of contact with said convex head of said first member, and said narrow section is in contact with said convex head and out of contact with said concave surface of said second member.

20. The bi-axial prosthetic joint of claim 19 wherein said wide section is located radially outward in the structure of said ring bearing and said narrow section is located radially inward.

* * * * *